United States Patent [19]
Kesling

[11] Patent Number: 5,057,012
[45] Date of Patent: Oct. 15, 1991

[54] MOLAR TUBE APPLIANCE FOR A LIP BUMPER OR A FACE BOW

[75] Inventor: Christopher K. Kesling, LaPorte, Ind.

[73] Assignee: TP Orthodontics, Inc., Westville, Ind.

[21] Appl. No.: 632,473

[22] Filed: Dec. 21, 1990

Related U.S. Application Data

[63] Continuation-in-part of Ser. No. 460,287, Jan. 3, 1990, abandoned.

[51] Int. Cl.$^5$ .............................................. A61C 3/00
[52] U.S. Cl. ........................................... 433/17; 433/5
[58] Field of Search ..................................... 433/5, 17

[56] References Cited

U.S. PATENT DOCUMENTS

| | | | |
|---|---|---|---|
| 986,076 | 3/1911 | Montag | 433/17 |
| 1,014,030 | 1/1912 | Angle | 433/17 |
| 1,429,749 | 9/1922 | Maeulen et al. | 433/17 |
| 3,055,110 | 9/1962 | Kesling | 433/17 |
| 3,494,034 | 2/1970 | Kesling | 433/17 |
| 3,526,961 | 9/1970 | Kesling | 433/17 |
| 3,815,238 | 6/1974 | Wallshein | 433/17 |
| 3,874,080 | 4/1975 | Wallshein | 433/17 |
| 4,245,986 | 1/1981 | Andrews | 433/5 |
| 4,378,210 | 3/1983 | Yatabe | 433/5 |
| 4,431,410 | 2/1984 | Ruderman | 433/5 |
| 4,453,917 | 6/1984 | Nodai et al. | 433/5 |
| 4,669,980 | 6/1987 | Degnan | 433/17 |
| 4,741,696 | 5/1988 | Cetlin | 433/17 |
| 4,781,582 | 11/1988 | Kesling | 433/17 |
| 4,897,035 | 1/1990 | Green | 433/17 |

OTHER PUBLICATIONS

American Orthodontics Corporation Catalog, 1989, p. 77.

*Primary Examiner*—John J. Wilson
*Attorney, Agent, or Firm*—Lloyd L. Zickert

[57] ABSTRACT

A molar tube appliance including a molar or buccal tube for mounting on a molar and for receiving a lip bumper or a face bow, wherein the tube has a flared opening with the larger end of the opening being at the mesial end. The opening is structured to enhance insertion of the lip bumper or face bow by the patient particularly where the molar is adversely rotated.

11 Claims, 5 Drawing Sheets

U.S. Patent   Oct. 15, 1991   Sheet 1 of 5   5,057,012
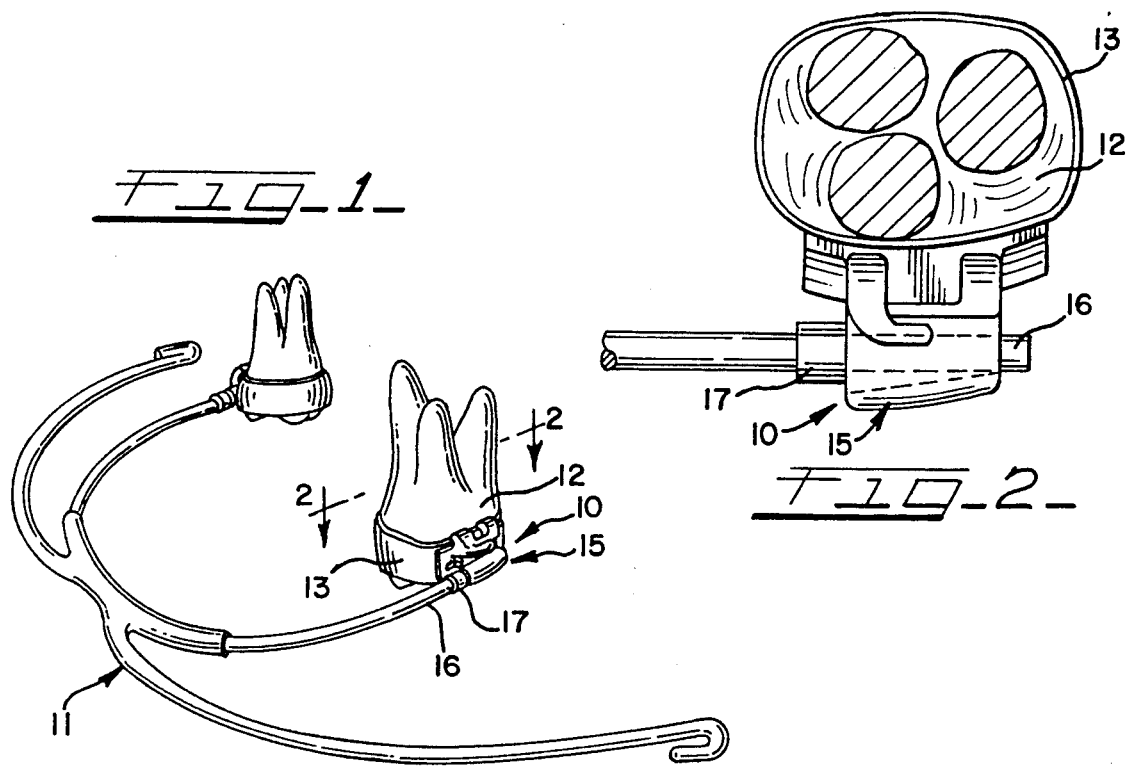
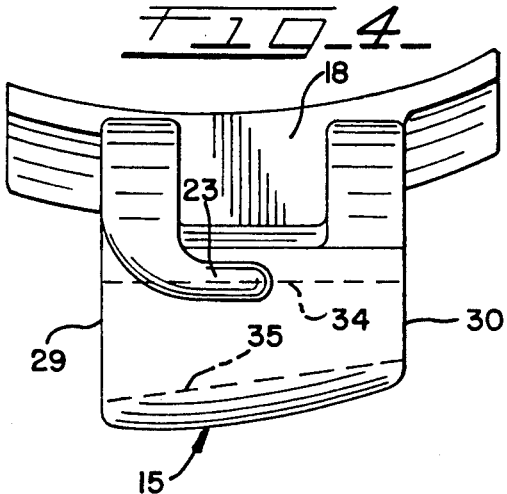
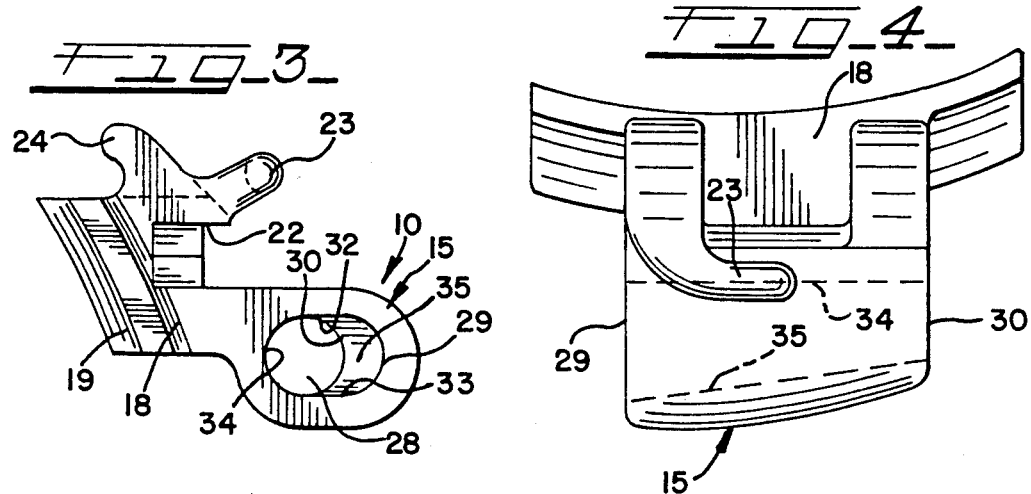
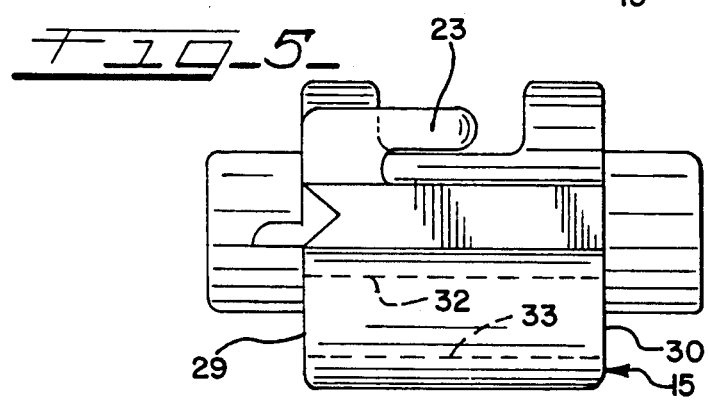

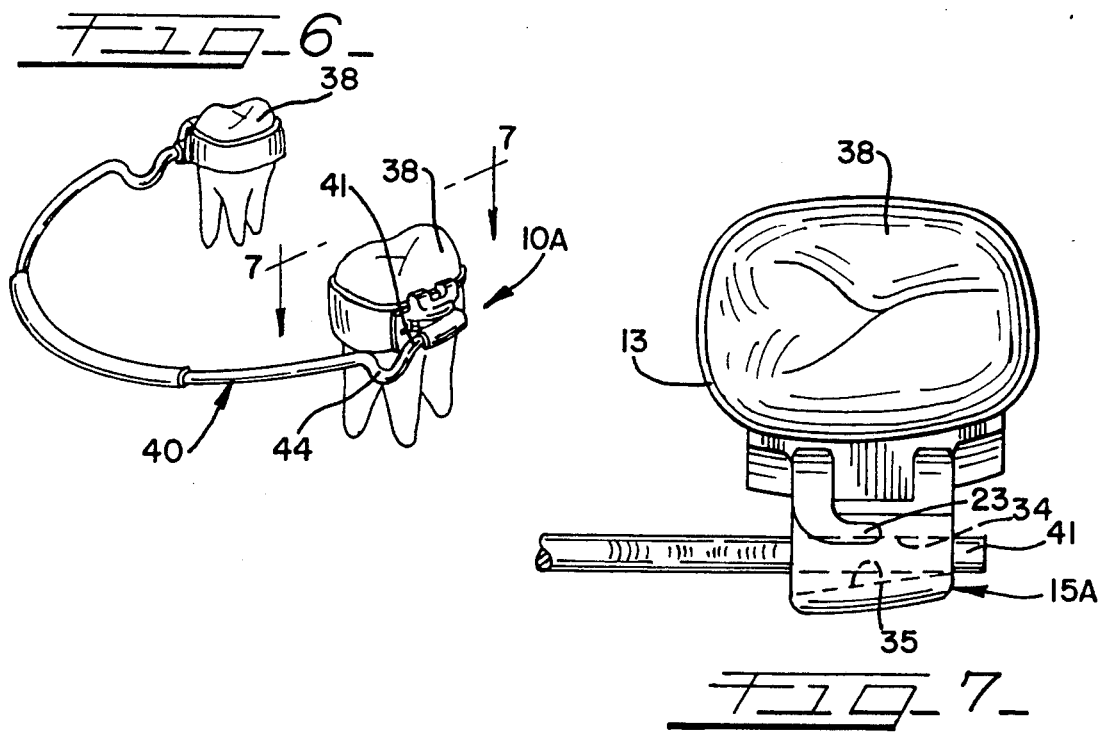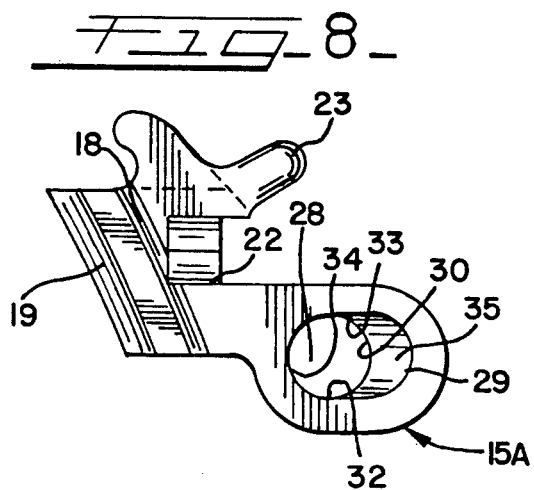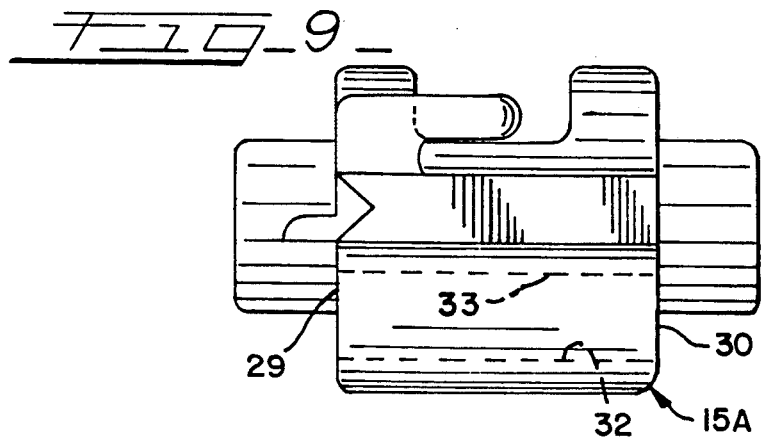

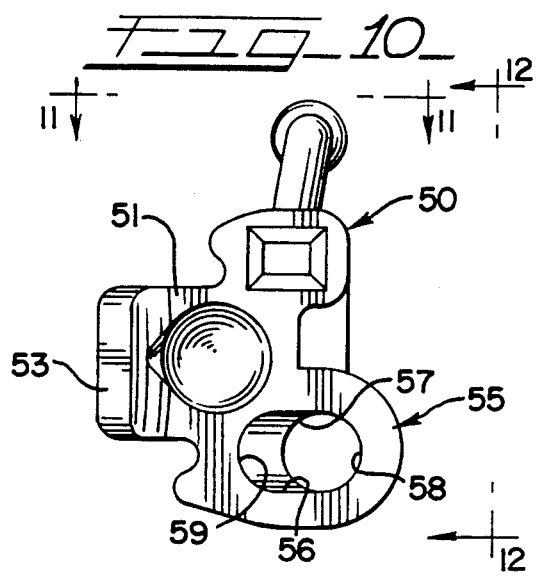
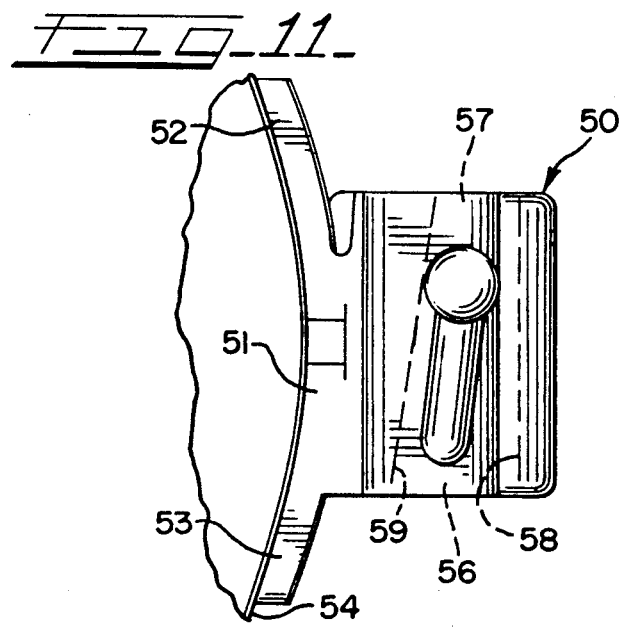
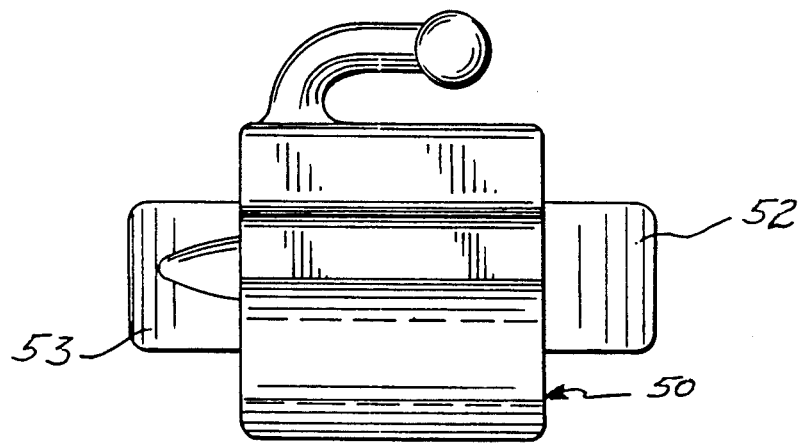

FIG.-13-
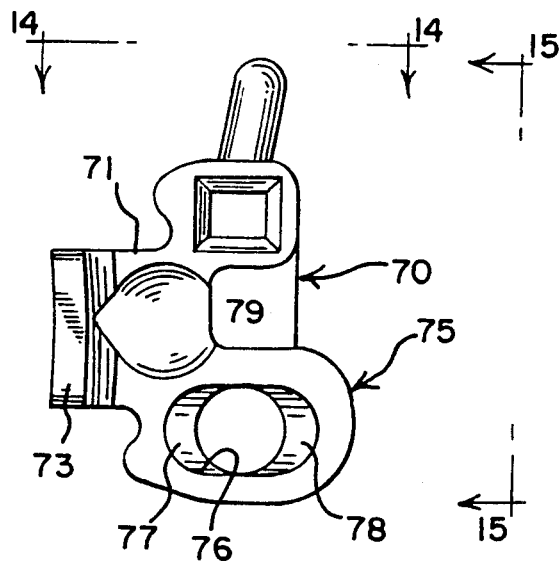
FIG.-14-
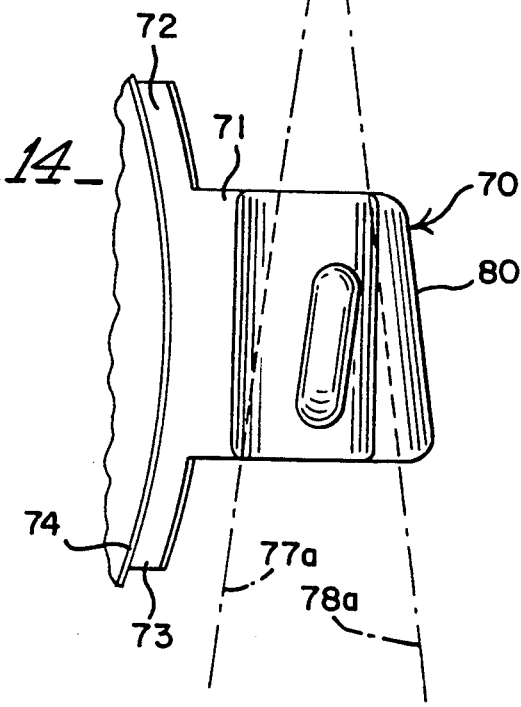
FIG.-15-
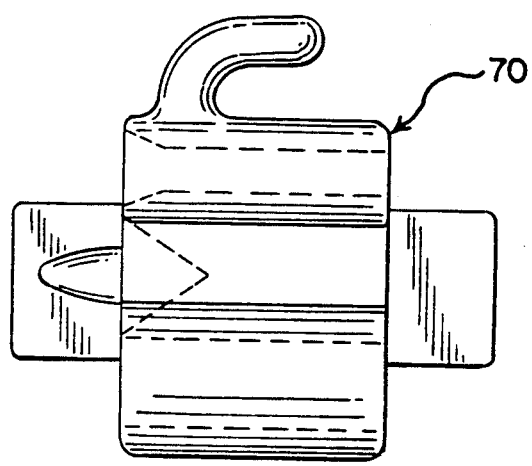

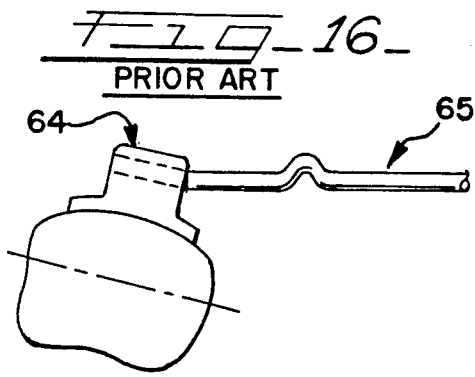
FIG_16_ PRIOR ART
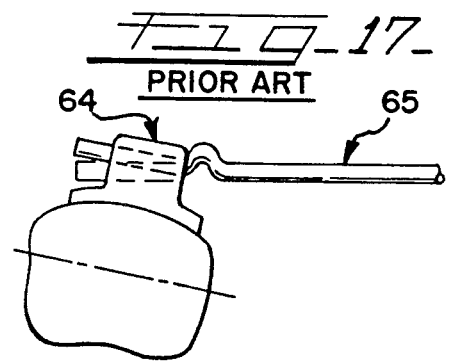
FIG_17_ PRIOR ART
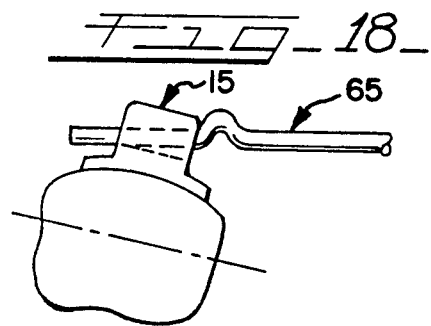
FIG_18_
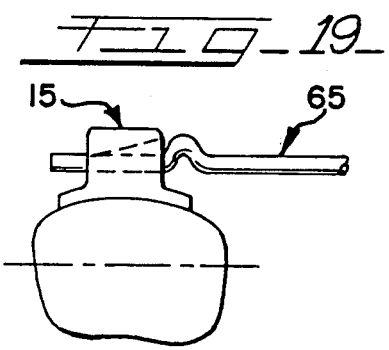
FIG_19_
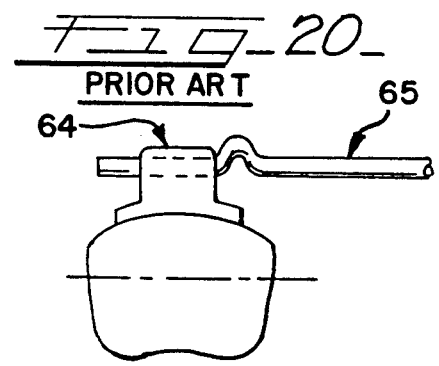
FIG_20_ PRIOR ART
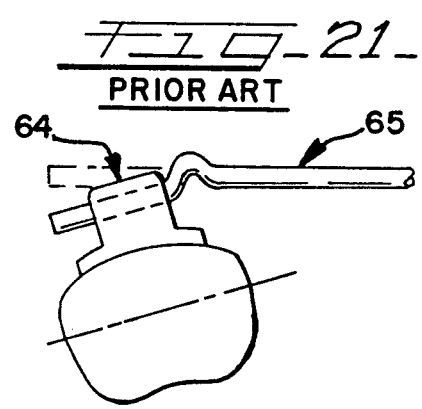
FIG_21_ PRIOR ART
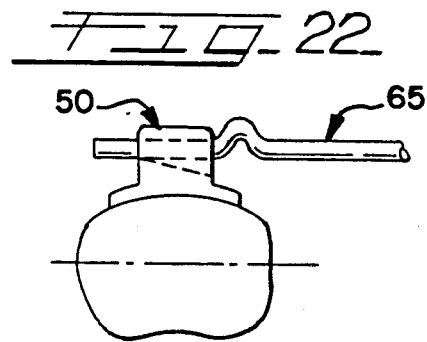
FIG_22_
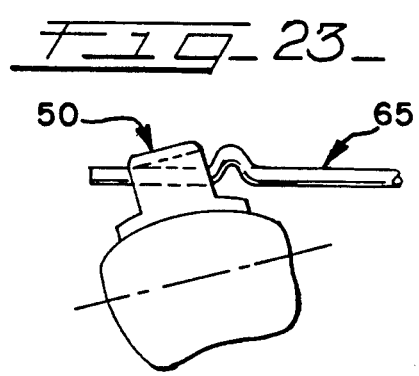
FIG_23_

MOLAR TUBE APPLIANCE FOR A LIP BUMPER OR A FACE BOW

DESCRIPTION

This application is a continuation-in-part application of my copending application Ser. No. 07/4 60,287, filed Jan. 3,1990, now abandoned.

This invention relates in general to a buccal tube appliance for use in orthodontic treatment, and more particularly to a molar tube appliance having a tube for a lip bumper or a face bow structured to greatly enhance the insertion of the lip bumper or face bow by the patient particularly where one or more of the molars are adversely rotated, and still more particularly to a buccal tube for a lip bumper or a face bow having an insertion end opening that is substantially larger than the wire end of the lip bumper or face bow and a distal end which mates with the lip bumper or face bow.

BACKGROUND OF THE INVENTION

Heretofore, buccal tubes for receiving the distal ends of a lip bumper or a face bow have been generally sized with a uniformly dimensioned opening between the mesial and distal and which closely receives the lip bumper or face bow end such as shown in U.S. Pat. No. 4,378,210.

The placement of a lip bumper or a face bow is nearly always done by the patient. The only exception is when the patient is visiting his orthodontist and the orthodontist is providing instructions on how to place the appliance. Since the face bow or lip bumper tubes have always been sized to closely receive the face bow or lip bumper ends, difficulty is often experienced by the patient in placement of the lip bumper or face bow as the size of the wire used for a lip bumper or a face bow is substantially equal to the size of the opening in the buccal tube which receives that end. These difficulties often lead to causing injuries in the mouth where the distal ends of the lip bumper or face bow impingedly engages and injures the tissues of the mouth.

It has also been desirable for many years to distally offset molar headgear tubes, but difficulty is experienced in mounting because the headgear face bows include arms or ends that are too stiff to insert into the standard molar tubes and then the ends of the arms must be bent to permit insertion.

It has been known to taper part of the inner end of the buccal tube such as shown in FIG. 3 of U.S. Pat. No. 3,874,080. Such a structure produces a lip or edge along the opening which could produce a hangup on insertion of a lip bumper or face bow end and result in accidental "bounce back" and then an injury to the soft tissues in the mouth. When it is considered that the patient must be responsible for insertion of the distal ends of a lip bumper or face bow, and further that the patient is not an expert in handling such an operation as opposed to a professional, the chance of accidental injury is substantially greater. Therefore, it is important to reduce this hazard in order to improve the quality of orthodontic treatment and the cooperation of a patient, and safer to place a lip bumper or face bow by the patient particularly when one or both molars are adversely rotated. It will be appreciated that those patients sensitive to mouth injury and wanting to avoid such injury may not use the lip bumper or face bow, thereby completely defeating the purpose of these appliances and ultimately lengthening or completely defeating orthodontic treatment.

SUMMARY OF THE INVENTION

The buccal tube appliance of the present invention overcomes the heretofore known deficiencies of heretofore known buccal tubes used for receiving the distal ends of a lip bumper, or the distal ends of a face bow of a headgear appliance so that it is safer and easier for a patient to insert the ends or arms of a face bow or lip bumper.

The present invention relates to a molar or buccal tube appliance that is particularly suitable for receiving the distal ends of a lip bumper or a face bow which will materially reduce the chance of injury to soft mouth tissues, thereby assuring better patient cooperation in the use of the appliance and ultimately better treatment results. Further, treatment time would be reduced. Also, the present invention makes it possible to distally offset headgear tubes without impairing the ability to insert the face bow. For the first time, because of the present invention, it is possible to manufacture a molar or buccal tube with a distal offset, this being a desirable and unique feature.

It is therefore an object of the present invention to provide a new and improved molar or buccal tube appliance for use with a lip bumper, or a face bow of a headgear system to make it easier and safer for a patient to insert the arms or ends of the face bow or lip bumper particularly when one or both of the molar teeth are adversely rotated.

A further object of the invention is in the provision of a molar or buccal tube appliance for receiving the distal ends of a lip bumper or a face bow which greatly enhances the insertionability of the distal ends of the lip bumper or face bow by the patient, thereby assuring better patient cooperation and better treatment results.

Another object of the present invention is in the provision of a molar or buccal tube appliance for a lip bumper or a face bow wherein the inlet end of the tube is enlarged greatly over the size of the distal ends of a lip bumper or a face bow to facilitate the insertion of the distal ends.

Still another object of the present invention is in the provision of a molar or buccal tube appliance for use with a lip bumper or a face bow which has a flared opening and an inlet end larger than the size of the lip bumper or facebow wire to greatly enhance the insertion of the distal end of a lip bumper or a face bow.

A further object of the invention is to provide a molar headgear tube that can be distally offset and still allow easy insertion of a face bow.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of a face bow having its distal ends received by a molar or buccal tube appliance of the present invention;

FIG. 2 is an enlarged top plan view of the molar or buccal tube appliance of the present invention and showing the relation between a distal end of the face bow and the opening in the buccal tube;

FIG. 3 is a still further enlarged mesial elevational view of the molar or buccal tube appliance of the present invention;

FIG. 4 is an enlarged top plan view or gingival view of the appliance of FIG. 3;

FIG. 5 is a buccal elevational view of the appliance of FIG. 3;

FIG. 6 is a perspective view like FIG. 1 and illustrating the use of a lip bumper with molar or buccal tube appliances according to the present invention;

FIG. 7 is an occlusally looking view in enlarged form of the molar or buccal tube appliance of FIG. 6 and showing its relation to a tooth and taken generally along line 7—7 of FIG. 6;

FIG. 8 is a mesial elevational view in still further enlarged form of the appliance shown in FIGS. 6 and 7;

FIG. 9 is a buccal elevational view of the appliance shown in FIG. 8;

FIG. 10 is another embodiment of the invention and an elevational view of a molar tube appliance according to the invention for an upper left molar and looking at the mesial end;

FIG. 11 is a top plan view of the appliance of FIG. 10 looking along line 11—11 in the direction of the arrows;

FIG. 12 is a buccal view of the appliance of FIG. 10 looking along line 12—12 in the direction of the arrows;

FIG. 13 is an elevational view of another embodiment of the invention for an upper left molar and looking at the mesial end;

FIG. 14 is a top plan view of the appliance in FIG. 13 looking along line 14—14 in the direction of the arrows;

FIG. 15 is a buccal view of the appliance of FIG. 13 looking along the line 15—15 in the direction of the arrows;

FIG. 16 is a view of the prior art molar tube mounted on a mesially rotated molar;

FIG. 17 illustrates the engagement of the face bow into the prior art tube illustrated in FIG. 16 and the necessity of bending the end in order to enable insertion where the end is bent in full lines and shown in straight position in dotted lines as illustrated in FIG. 16;

FIG. 18 illustrates the buccal tube of the present invention in schematic a set forth in FIGS. 1 to 9 and the ability to easily and safely insert the face bow or lip bumper end or arm when the molar tooth is mesially rotated;

FIG. 19 illustrates the manner in which this buccal tube corrects the adverse rotation of the molar as distally directed forces are applied by the face bow or lip bumper to the tube and attached tooth without modifying the end of the face bow or lip bumper;

FIG. 20 is a schematic view of the prior art molar tube mounted on a molar tooth that requires mesial buccal rotation to produce the distal offset that is generally desired with maxillary molars;

FIG. 21 shows the manner in which the end of the face bow must be bent to produce this desired rotation; the end is bent in full lines and shown in straight position in dotted lines as illustrated in FIG. 20;

FIG. 22 is a view of the embodiment of this illustration shown in FIGS. 10 to 12 mounted on a molar tooth that requires mesial buccal rotation to produce the desired distal offset; and FIG. 23 shows the manner in which this tube produces the desired rotation without modifying the end of the face bow as distally directed force is applied by the face bow to the tube and attached tooth.

DESCRIPTION OF THE INVENTION

The present invention is to a molar or buccal tube appliance for receiving the distal end of a lip bumper or a face bow, it being appreciated that tubes for receiving the lip bumper would be generally mounted on the lower molars, while tubes for receiving a face bow would be generally mounted on the upper molars, as this is the normal use of these appliances. It will also be appreciated that the buccal tube will normally be a part of a combination appliance that would have one or more additional molar or buccal tubes for receiving a main archwire and/or an auxiliary archwire and also optionally a hook for attachment of one end of an elastic which would then be used to attach a hook on a lip bumper for maintaining the bumper in position. It will also be appreciated that the lip bumper is generally used to apply distal forces to the lower molars, while a face bow would be generally used to apply distal forces to the upper molars.

The molar or buccal tube appliance of the invention is unique in that it facilitates the insertion of a distal end of a lip bumper or a face bow by a patient. During treatment or otherwise, unrestrained molars tend to move forward and to nearly always rotate mesially. Only on rare occasions will a molar rotate distally. So, it is not uncommon to see molars adversely rotated mesially, and then it is impossible to completely insert a face bow or lip bumper in a mesially rotated standard buccal tube, as illustrated in FIG. 19. This then necessitates special adjustments of the face bow or lip bumper or other special procedures before the lip bumper or face bow can be easily inserted by the patient. Here, it also will be appreciated that a patient is not an expert like a professional, and therefore an accommodation is preferable to facilitate the placement by a patient of a lip bumper or face bow. Improper procedures in placement would normally result in injury to soft tissues that could be very painful for the patient and which might suggest to the patient that such injury could be avoided by nonuse of the face bow or lip bumper. Such nonuse or noncooperation results in prolonging and/or preventing good results during orthodontic treatment.

The molar or buccal tube appliance of the invention includes a flared opening which facilitates the insertion of the lip bumper or face bow to make it easier for a patient to place the lip bumper or face bow. Thus, proper placement of the lip bumper permits pressure on the lip bumper from the lip to apply a distal force to the molars on which the lip bumper tubes are attached. Similarly, proper placement of a face bow used in a headgear will allow proper application of distal forces to the molar teeth on which the headgear tubes are attached. Where molars are adversely rotated, the present invention allows complete insertion of the face bow or lip bumper. Additionally, where molars are mesially rotated, distally directed forces by the face bow or lip bumper applied to the buccal surfaces of the molars provide the desired disto-lingual rotation without the need for palatal bars, a series of leveling archwires, or having to repeatedly adjust the head bows or lip bumpers with bending procedures. It will further be understood that when using lip bumper tubes, which would accommodate a lip bumper, they are used on the lower arch and the tubes are generally disposed gingivally to the main archwire tube. The position of the headgear tubes for use in receiving a face bow on the upper arch would generally be positioned occlusally to the molar tube for the main archwire, as seen in FIG. 1, but it may be positioned gingivally if so desired.

The molar or buccal tube of the invention in one embodiment includes an opening extending through the tube which has a larger mesial end then distal end and is flared from the distal end to the mesial end so that a larger end is at the mesial of the tube than at the distal. More tolerance is thereby provided at the mesial end for ease in receiving the distal end of a lip bumper or face bow.

The form of the flaring in the tube in one embodiment is defined by inclining the outer wall of the tube or the buccal wall of the opening when maintaining the lingual wall parallel to the buccal tooth surface. The distal end of the opening is sized to closely fit the distal end of the lip bumper or face bow so as to assist in controlling rotation of the molar on which the tube is mounted. Thus, the lingual wall of the opening is substantially parallel to the base of the buccal tube appliance, while the buccal wall of the opening is inclined along a horizontal axis where the included angle is at the distal end. The vertical height of the tube is such as to closely receive the distal end of the face bow or lip bumper to control tipping of the tooth and to eliminate any vertical tolerance, or at least keep it to a minimum.

In another embodiment, the buccal wall is parallel to the base, while the lingual wall is inclined to coact with the buccal wall and define the flared hole in the tube.

In still another embodiment, both buccal and lingual walls are inclined to the base to provide the maximum inlet or mouth to the flared hole extending through the tube.

Referring now to the drawings, and particularly to FIG. 1 and the embodiment of FIGS. 1 to 9, it will be seen that a pair of molar or buccal tubes according to the invention are respectively mounted on molar teeth. It will be appreciated that the tubes will generally be formed for the right and left teeth. The appliance is generally designated by the numeral 10 and as shown in FIG. 1 is formed for mounting on the upper teeth so that it can be used for receiving the distal ends of a face bow 11 of a headgear system. The appliance is mounted on a molar tooth 12 by it being first preferably secured to a band 13 that is suitably cemented to the tooth. For purposes of the present invention, it is only necessary to specifically describe one of the appliances and in this instance it will be the left appliance for a left molar.

The appliance 10 includes the molar or buccal tube 15 of the invention which will receive the distal end of the face bow 11, and in this case the distal end portion 16, which would be in the form of a round wire or bar of normally 0.045 inches. A stop 17 is provided on the end 16 in order to limit the position of the distal end so that a distal force can be applied by the headgear.

The appliance includes a base 18 from which the buccal tube 15 extends buccally, and it will be appreciated that the base is provided with a lingually facing attaching surface 19 that is suitably secured to the band 13 such as by welding or the like. Additionally, the appliance includes a standard edgewise archwire slot 22 that may have a temporary outer shield to define a tube for a main archwire and which can be removed to thereafter have the archwire suitably act on the appliance in the treatment process. Additionally, the appliance may include a hook 23 and tie wings 24, as shown, which can coact with the tube 15 when it is desired to secure an archwire in the slot 22 by means of a suitable ligature.

The buccal tube 15 includes an elongated and longitudinally extending opening 28 having a mesial end 29 and a distal end 30. The opening further includes upper and lower generally parallel extending walls 32 and 33, an inner lingual wall 34 that extends substantially parallel to the base 18 and an outer buccal wall 35 that is inclined relative to the inner wall 34 such as to define a flaring extending from the distal end to the mesial end.

It will be further appreciated that the inlet end or insertion end 29 of the tube is oval shaped, while the outlet end or distal end 30 is round. The distal end 30 would also be sized to closely receive the distal end of the face bow so that rotational control would be obtained. Further, the long axis of the oval end 29 is generally horizontally extending, while the vertical dimension of the end 29 is of substantially the same dimension as the diameter of the round opening 30 so as to prevent a looseness along the vertical axis of the tubular opening. When the very end of the face bow is inserted, it will be guided along the inclined buccal wall 35, as it is moved through the opening and through the distal end 30, after which it will essentially contact or engage the lingual wall 34 by virtue of the horizontal width of the mesial end 29. It will be appreciated that it will facilitate the ease of insertion of the face bow by the patient and minimize the accidental engagement of the very ends of the face bow with soft tissues that could injure the tissues.

As seen particularly in FIG. 4, the inclined inner buccal wall 35 of the opening defines an included angle with the inner lingual wall 34 at the distal end of the tube. More room is provided horizontally to facilitate the horizontal width of the tube at the mesial end and to further facilitate the insertion of the face bow.

Referring now to FIGS. 6 to 9, an appliance having a buccal tube according to the invention for use with a lip bumper is illustrated, and here it will be noted that the lip bumper tubes are mounted on lower molars 38 as the lip bumper is used for applying distal forces to lower molars. The appliance for lower molars is generally indicated by the numeral 10A and includes a lip bumper tube 15A which generally is formed like the face bow or headgear tube in the embodiment of FIGS. 1 to 5 except that the lip bumper tube is gingivally positioned relative to the main archwire tube or slot. The lip bumper 40 includes distal ends 41 that are of round wire or bar, also usually of 0.045 inches in diameter, to be received by the lip bumper tube 15A which has an opening of the same configuration as the opening in the face bow tube 15. Accordingly, some of the numerals used on the headgear tube 15, designating the same parts will be used on the tube 15A. Additionally, the lip bumper includes a bend or stop 44 that can function as a stop to prevent the lip bumper from moving distally beyond the lip bumper tube.

Otherwise, the lip bumper tube operates in the same fashion as the face bow tube in providing an enlarged mesial end for receiving the distal end of the lip bumper and a closely fitting distal end for controlling the rotation of the tooth.

Referring now to the embodiment in FIGS. 10 to 12, another embodiment of the invention is illustrated which is a buccal or molar tube appliance 50 for an upper left molar for receiving a face bow. This appliance includes a base 51 having attaching flanges 52 and 53 that serve to assist in suitably attaching the appliance to a molar band 54. At the occlusal end of the appliance 50, a molar or buccal tube 55 according to the invention includes at the mesial end an enlarged opening 56 having a buccal-lingual dimension substantially greater than the diameter of the face bow wire to facilitate insertion of the face bow. Insertion of the face bow wire is guided along the lingual wall of the tube. While the appliance 50 is shown mounted with the molar tube at the occlusal, it should be appreciated the appliance could be mounted with the molar tube at the gingival if desired.

The buccal tube 55 further includes an opening 57 at the distal end of the tube which is sized to be only slightly larger than the size of the face bow distal end so as to closely receive the wire end of the face bow. Further, the opening through the tube includes a buccal wall 58 that extends substantially parallel to the attaching flanges 52 and 53 and therefore substantially parallel to the buccal face of the tooth when the appliance is mounted on the tooth. The tube has a lingual wall 59 which is angularly related to the attaching flanges and the buccal face of the tooth such that the tube 55 is effectively distally offset from the tooth when it is squarely mounted on the buccal face of the molar, as can be best seen in FIG. 11. The vertical dimension of the tube opening is only slightly greater than the diameter of the face bow ends so as to closely control vertical movement between the molar or buccal tube and the face bow. Thus, it is possible to easily insert the face bow ends into the buccal tube when a tooth is adversely rotated such as generally illustrated in FIGS. 22 and 23.

As previously mentioned, where the condition exists as shown in FIG. 21 with the standard molar or buccal tube, where the wire ends cannot be inserted without being adjusted, the desired disto-lingual rotation can only be produced by use of several leveling archwires or a series of adjustments made to the face bow or lip bumper. Also, where it has heretofore been desired to rotate such molars by use of palatal arch bars, it is necessary to repeatedly adjust the arch bars during rotation. Such adjustment procedures are not necessary with the present invention because the face bow or lip bumper 65 is inserted as seen in FIG. 19 so the stop engages the tube and the distal forces of the face bow will cause the malrotated teeth to rotate distolingually in order to place the molars in the proper orientation.

The buccal tube opening of the embodiment of FIGS. 10 to 12 is essentially identical to that of the embodiment of FIGS. 1 to 9 with the exception that the tube is distally offset rather than mesially offset, thereby providing the advantage of being able to have a distally offset buccal tube and the ease of insertion not heretofore possible. This is illustrated in FIG. 20 where a conventional molar or buccal tube 64 is mounted on a molar that required mesiobuccal rotation to produce the desired distal offset. FIG. 21 illustrates the manner in which the end of the face bow must be bent to produce the desired mesio-buccal rotation and consequent distal offset when using the prior art tube illustrated in FIG. 20. However, the present invention as depicted by the buccal tubes 50 in FIGS. 22 and 23 illustrates the ease with which the desired mesio-buccal rotation and consequent distal offset can be produced without bending the end of the face bow as distally directed forces are applied to this tube and the attached tooth.

Another embodiment of the invention is shown in FIGS. 13 to 15, which differs from the earlier embodiments in that both lingual and buccal walls of the buccal tube hole or opening are inclined or at an angle to the base of the appliance. Additionally, the overall profile differs when looking at the tube from the gingival or occlusal. This buccal tube appliance is generally designated by the numeral 70 and the embodiment illustrated is for an upper divergeleft molar.

The buccal tube appliance 70 includes a base 71 having attaching flanges 72 and 73 for suitably attaching the appliance to a molar band 74, as seen particularly in FIG. 14. A molar or buccal tube 75 is disposed at the occlusal end of the appliance 70. The molar tube 75 includes a hole or opening therethrough for receiving an arm or end of a face bow or a lip bumper and is provided at the mesial end with an enlarged opening or mouth 76 having a buccal-lingual dimension that is substantially greater than the diameter of the face bow wire to greatly facilitate insertion of the face bow, particularly by a patient where one or both molars are adversely rotated. The buccal tube hole includes an inclined lingual wall 77 and an inclined buccal wall 78, the two coacting to define a flared hole extending clear through the buccal tube as particularly illustrated by the extended dashed lines 77a and 78a in FIG. 14. The inclined lingual or inside wall extends at an angle to the base with the included angle being at the mesial end of the opening through the tube; and the inclined buccal or outside wall extends at an angle to the base with the included angle being at the distal end of the opening through the tube. No matter which way the molar tooth would be rotated, and where the appliance 70 is mounted squarely on the molar tooth, that is, on and parallel to the buccal face of the tooth, the opening 76 of the hole in the buccal tube will enhance the easy insertion of the face bow end or arm and guide it either along the lingual wall 77 or the buccal wall 78 until it exits the distal opening 79 of the tube. Further, the wide mouth of the buccal tube opening at the mesial end and the inclined walls which converge toward the distal end allow the molar tooth to be easily rotated into a proper position during the wearing of the face bow. The opening 79 of the hole at the distal end is such as to mate with the size of the face bow end or arm and to provide the type of control desired during the wearing of the face bow. Thus, it can be appreciated that this embodiment will even provide a larger opening buccolingually for receiving the end of a face bow to further facilitate safe and easy insertion by the patient. In order to structure the hole or opening of the tube so that both lingual and buccal walls are inclined and make the tube structurally sound, the buccal edge 80 is inclined to the base unlike the buccal edges of the previous embodiments which are substantially parallel to the base. Further, the edge 80 is substantially parallel to the buccal wall 78a.

In view of the foregoing, it will be appreciated that the molar or buccal tube of the present invention is particularly useful for lip bumpers and face bows to enhance the safe insertion of the lip bumper or face bow by the patient and produce better patient cooperation and treatment results.

It will be understood that modifications and variations may be effected without departing from the scope of the novel concepts of the present invention, but it is understood that this application is to be limited only by the scope of the appended claims.

The invention is hereby claimed as follows:

1. A molar tube for a lip bumper or a face bow comprising, a base having a lingually facing attaching surface for attaching to a tooth, an elongated mesialdistally extending tubular body projecting buccally from said base, said body including an opening therethrough for receiving the distal ends of a lip bumper or a face bow and having an inside lingual wall and an outside buccal wall, said opening being flared from the distal end to the mesial end such that the mesial end is larger than the distal end and of a size substantially larger than the distal end of a lip bumper or a face bow, said distal end of the opening being round and sized to closely receive the distal end of the lip bumper or face bow to provide lateral control, said mesial end being oval and having a vertical dimension to closely receive the distal end of the lip bumper or face bow to control tipping, and the long axis of the oval mesial end extending generally horizontally, whereby insertion of a distal end of a lip bumper or a face bow is greatly enhanced.

2. The buccal tube of claim 1, wherein the inside lingual wall of said opening is generally parallel to the base and the outside buccal wall of said opening extends at an angle to the base with the included angle being at the distal end of said opening.

3. The buccal tube of claim 1, wherein the outside buccal wall of the opening is generally parallel to the base and the inside lingual wall of said opening extends at an angle to the base with the included angle being at the mesial end of the opening.

4. The buccal tube of claim 1, wherein the outside buccal wall of said opening extends at an angle to the base with the included angle being at the distal end of the opening, and the inside lingual wall of said opening extends at an angle to the base with the included angle being at the mesial end of the opening.

5. The buccal tube of claim 1, wherein the opening is distally offset such that the lingual wall extends at an angle to the base.

6. The buccal tube of claim 1, wherein the inside lingual wall of the opening is distally offset from the base, and the outside buccal wall of the opening is parallel from the base.

7. In combination with a base having a buccal tube for receiving a main archwire, said buccal tube adapted to be mounted on the buccal face of a molar tooth, means for receiving a distal end of a lip bumper or a face bow, the improvement in said means which includes an elongated tube carried by said base having a mesial-distally extending opening, said opening having a mesial end and a distal end and being flared from the distal end to the mesial end, the mesial end being substantially larger than the distal end and oval shaped to facilitate insertion of the lip bumper or face bow particularly when the molar tooth is adversely rotated, and the distal end being round to closely receive the distal end of the lip bumper or face bow and provide lateral control, the long axis of the oval-shaped mesial end extending generally horizontally and the vertical dimension of the opening being sized to closely receive the distal end of the lip bumper or face bow to control tipping.

8. The means of claim 7, wherein the lingual wall of the opening is generally parallel to the base and the buccal wall of the opening extends at an angle to the base with the included angle being at the distal end of the opening.

9. The means of claim 7, wherein the opening is distally offset such that the lingual wall extends at an angle to the base.

10. The means of claim 7, wherein the outside wall of the opening is generally parallel to the base and the inside wall of said opening extends at an angle to the base with the included angle being at the mesial end of the opening.

11. The means of claim 7, wherein the outside buccal wall of said opening extends at an angle to the base with the included angle being at the distal end of the opening, and the inside lingual wall of said opening extends at an angle to the base with the included angle being at the mesial end of the opening.

* * * * *